United States Patent
Munjal et al.

(10) Patent No.: US 12,168,000 B2
(45) Date of Patent: Dec. 17, 2024

(54) METHODS OF TREATING PAIN

(71) Applicant: Scilex Holding Company, Palo Alto, CA (US)

(72) Inventors: Sagar Munjal, Raleigh, NC (US); Anirudh Gautam, Raleigh, NC (US)

(73) Assignee: SCILEX HOLDING COMPANY, Palo Alto, CA (US)

( * ) Notice: Subject to any disclaimer, the term of this patent is extended or adjusted under 35 U.S.C. 154(b) by 0 days.

(21) Appl. No.: 17/562,229

(22) Filed: Dec. 27, 2021

(65) Prior Publication Data

US 2022/0202776 A1    Jun. 30, 2022

Related U.S. Application Data (60) Provisional application No. 63/131,172, filed on Dec. 28, 2020.

(51) Int. Cl.
*A61K 31/415* (2006.01)
*A61P 29/00* (2006.01)

(52) U.S. Cl.
CPC .......... *A61K 31/415* (2013.01); *A61P 29/00* (2018.01)

(58) Field of Classification Search
CPC .... A61K 31/415; A61K 47/14; A61K 9/0095; A61K 31/635; A61K 9/0053; A61K 9/48; A61P 29/00; A61P 23/00; A61P 25/00
USPC ........................................................ 514/415
See application file for complete search history.

(56) References Cited

U.S. PATENT DOCUMENTS

| | | | |
|---|---|---|---|
| 5,456,923 | A | 10/1995 | Nakamichi et al. |
| 5,466,823 | A | 11/1995 | Talley et al. |
| 5,760,068 | A | 6/1998 | Talley et al. |
| 5,993,858 | A | 11/1999 | Crison et al. |
| 6,057,289 | A | 5/2000 | Mulye |
| 6,096,338 | A | 8/2000 | Lacy et al. |
| 6,248,363 | B1 | 6/2001 | Patel et al. |
| 6,267,985 | B1 | 7/2001 | Chen et al. |
| 6,280,770 | B1 | 8/2001 | Pather et al. |
| 6,294,192 | B1 | 9/2001 | Patel et al. |
| 6,383,471 | B1 | 5/2002 | Chen et al. |
| 6,436,430 | B1 | 8/2002 | Mulye |
| 6,451,339 | B2 | 9/2002 | Patel et al. |

(Continued)

FOREIGN PATENT DOCUMENTS

| | | | |
|---|---|---|---|
| CA | 2987272 A1 * | 12/2016 | .......... A61K 31/415 |
| JP | 2003503440 A | 1/2003 | |

(Continued)

OTHER PUBLICATIONS

Moore et al , Tolerability and adverse events in clinical trials of celecoxib in osteoarthritis and rheumatoid arthritis: systematic review and meta-analysis of information from company clinical trial reports, Arthritis Research & Therapy, vol. 7 No. 3 , Mar. 24, 2005, p. R644-R665 (Year: 2005).*

(Continued)

*Primary Examiner* — Taylor V Oh
(74) *Attorney, Agent, or Firm* — Fortem IP LLP (57) ABSTRACT

The present application relates to a method of providing a therapeutic regimen for the treatment of pain, wherein said method comprises administering an oral liquid pharmaceutical composition comprising celecoxib or a pharmaceutically acceptable salt thereof to a subject in need thereof.

15 Claims, 3 Drawing Sheets

Pain intensity difference (PID) scores over time for example-1, example-2, and example-3 over CELEBREX® 200 mg and CELEBREX® 400 mg oral capsules.

(56) References Cited

U.S. PATENT DOCUMENTS

| | | | |
|---|---|---|---|
| 6,531,139 | B1 | 3/2003 | Gao et al. |
| 6,555,558 | B2 | 4/2003 | Chen et al. |
| 6,569,463 | B2 | 5/2003 | Patel et al. |
| 6,579,895 | B2 | 6/2003 | Karim et al. |
| 6,638,522 | B1 | 10/2003 | Mulye |
| 6,720,001 | B2 | 4/2004 | Chen et al. |
| 6,761,903 | B2 | 7/2004 | Chen et al. |
| 6,923,988 | B2 | 8/2005 | Patel et al. |
| 6,962,931 | B2 | 11/2005 | Gumkowski et al. |
| 7,374,779 | B2 | 5/2008 | Chen et al. |
| 8,592,490 | B2 | 11/2013 | Legen et al. |
| 9,572,819 | B2 | 2/2017 | Baheti et al. |
| 9,750,756 | B2 | 9/2017 | Gao et al. |
| 9,795,620 | B2 | 10/2017 | Baheti et al. |
| 9,949,990 | B2 | 4/2018 | Baheti et al. |
| 10,376,527 | B2 | 8/2019 | Baheti et al. |
| 10,722,456 | B2 | 7/2020 | Munjal |
| 10,799,517 | B2 | 10/2020 | Baheti et al. |
| 2002/0006951 | A1 | 1/2002 | Hageman et al. |
| 2002/0028238 | A1 | 3/2002 | Karim et al. |
| 2002/0107250 | A1 | 8/2002 | Hariharan et al. |
| 2002/0142045 | A1 | 10/2002 | Kararli et al. |
| 2003/0105144 | A1 | 6/2003 | Gao et al. |
| 2003/0219477 | A1 | 11/2003 | Berthel et al. |
| 2003/0235596 | A1 | 12/2003 | Gao et al. |
| 2004/0175401 | A1 | 9/2004 | Pinkerton |
| 2006/0148877 | A1 | 7/2006 | Bernstein et al. |
| 2008/0009467 | A1 | 1/2008 | Henderson |
| 2010/0233272 | A1 | 9/2010 | Appel et al. |
| 2012/0171284 | A1 | 7/2012 | Gao et al. |
| 2012/0172341 | A1 | 7/2012 | Portillo Salido et al. |
| 2013/0072534 | A1 | 3/2013 | Videla Ces et al. |
| 2013/0296280 | A1 | 11/2013 | Park et al. |
| 2014/0050807 | A1 | 2/2014 | Leighton |
| 2015/0224121 | A1 | 8/2015 | Okumu et al. |
| 2015/0342893 | A1 | 12/2015 | Coulter et al. |
| 2016/0199392 | A1 | 7/2016 | Trieu |
| 2016/0346301 | A1 | 12/2016 | Baheti et al. |
| 2017/0119798 | A1 | 5/2017 | Baheti et al. |
| 2018/0008619 | A1 | 1/2018 | Baheti et al. |
| 2018/0200270 | A1 | 7/2018 | Baheti et al. |
| 2018/0200271 | A1 | 7/2018 | Baheti et al. |
| 2019/0224219 | A1 | 7/2019 | Baheti et al. |
| 2020/0352853 | A1 | 11/2020 | Munjal et al. |

FOREIGN PATENT DOCUMENTS

| | | |
|---|---|---|
| JP | 2004500427 A | 1/2004 |
| JP | 2007512373 A | 5/2007 |
| KR | 20130115650 A | 10/2013 |
| KR | 101413846 B1 | 6/2014 |
| KR | 20140100170 A | 8/2014 |
| MX | 349193 B | 7/2017 |
| WO | WO-0101960 A1 | 1/2001 |
| WO | WO-0178724 A1 | 10/2001 |
| WO | WO-0191750 A1 | 12/2001 |
| WO | WO-2004000284 A1 | 12/2003 |
| WO | WO-2004047752 A2 | 6/2004 |
| WO | WO-2005053612 A2 | 6/2005 |
| WO | WO-2007112274 A2 | 10/2007 |
| WO | WO-2008115572 A1 | 9/2008 |
| WO | WO-2010150144 A2 | 12/2010 |
| WO | WO-2015123272 A1 | 8/2015 |
| WO | WO-2016191744 A1 | 12/2016 |
| WO | WO-2017208069 A2 | 12/2017 |

OTHER PUBLICATIONS

Chavan, R. et al., "Role of solid carriers in pharmaceutical performance of solid supersaturable SEDDS of celecoxib," International Journal of Pharmaceutics, Nov. 1, 2015, vol. 495, No. 1, pp. 374-384.

Da Costa et al., "Effectiveness of non-steroidal anti-inflammatory drugs for the treatment of pain in knee and hip osteoarthritis: a network meta-analysis," The Lancet, May 2016, vol. 387, Issue 10033, pp. 2093-2210 [Retracted May 21, 2016].

International Search Report and Written Opinion in Intl. App. No. PCT/IB2017/000741, mailed Dec. 21, 2017, 19 pages.

International Search Report and Written Opinion in Intl. App. No. PCT/US2016/034844, mailed Aug. 29, 2016, 16 pages.

International Search Report and Written Opinion in Intl. App. No. PCT/IB2021/000946, mailed Jun. 14, 2022, 11 pages.

Kivitz, A. J., et al. "Comparative efficacy and safety of celecoxib and naproxen in the treatment of osteoarthritis of the hip," The Journal of International Medical Research, Dec. 2001, vol. 29, No. 6, pp. 467-479.

Loo, CY et al., "Randomised, open label, controlled trial of celocoxib in the treatment of acute migraine," Singapore Med J, Sep. 1, 2007, vol. 48, No. 9, pp. 834-839.

O'Hanlon et al., "NIR-labeled perfluoropolyether nanoemulsions for drug delivery and imaging," Journal of Flourine Chemistry, Feb. 7, 2012, vol. 137, pp. 27-33.

Peres et al., "Brief Communication Hemicrania Continua Responds to Cyclooxygenase-2 Inhibitors," Headache D, Jun. 1, 2002, vol. 42, pp. 530-531.

Reddy, B. et al., "Prevention of Colon Cancer by Low Doses of Celecoxib, a Cyclooxygenase Inhibitor, Administered in Diet Rich in w-3 Polyunsaturated Fatty Acids," Eur J Clin Pharmacol., 1995, vol. 47, No. 6, pp. 453-458.

Schachtel, BP et al., "Efficacy of low-dose celecoxib in patients with acute pain," J. Pain., Jul. 2011, vol. 12, No. 7, pp. 756-763.

Song et al., "In situ intestinal permeability and in vivo oral bioavailability of celecoxib in supersaturating self-emulsifying drug delivery system", Archives of Pharmacal Research, 2013, 37(5), 626-635.

Subramanian et al., "Formulation design of self-microemulsifying drug delivery systems for improved oral bioavailability of celecoxib", Biological & Pharmaceutical Bulletin, 2004, 27(12), 1993-1999.

Subramanian et al., "Topical Delivery of celecoxib using microemulsion," Biopharmacy, ACTA Poloniae Pharmaceutica—Drug Research, 2004, vol. 61, No. 5, pp. 335-341.

Taghdiri et al., "Celecoxib vs Prednisone for the Treatment of Withdrawal Headache in Patients with Medication Overuse Headache: A Randomized, Double-Blind Clinical Trial," Headache, Jan. 1, 2015, vol. 55, No. 1, pp. 128-135.

Tan et al., "Silica-Lipid Hybrid (SLH) Non-lipid Formulations for Optimising the Dose-Dependent Oral Absorption of Celecoxib," Pharmaceutical Research, May 11, 2011, vol. 28, No. 9, pp. 2273-2287.

Zvonar et al., "The Influence of Microstructure on Celecoxib Release from a Pharmaceutically Applicable System: Mygliol 812/ Labrasol/ Plurol Oleique/Water Mixtures," ACTA Chim Slov, 2009, vol. 56, pp. 131-138.

Non-Final Office Action in U.S. Appl. No. 16/938,564, mailed Nov. 15, 2021, 12 pages.

Non-Final Office Action in U.S. Appl. No. 15/167,922, mailed Oct. 3, 2016, 11 pages.

Non-Final Office Action in U.S. Appl. No. 15/374,951, mailed Mar. 14, 2017, 9 pages.

Non-Final Office Action in U.S. Appl. No. 15/607,216, mailed Oct. 19, 2017, 18 pages.

Non-Final Office Action in U.S. Appl. No. 15/607,216, mailed Mar. 7, 2019, 31 pages.

Non-Final Office Action in U.S. Appl. No. 15/712,415, mailed Oct. 26, 2017, 6 pages.

Non-Final Office Action in U.S. Appl. No. 15/922,170, mailed May 23, 2018, 5 pages.

Non-Final Office Action in U.S. Appl. No. 16/369,981, mailed Jun. 14, 2019, 20 pages.

Non-Final Office Action in U.S. Appl. No. 16/369,981, mailed Mar. 11, 2021, 21 pages.

Final Office Action in U.S. Appl. No. 15/607,216, mailed May 11, 2018, 23 pages.

Final Office Action in U.S. Appl. No. 15/607,216, mailed Dec. 30, 2019, 10 pages.

(56) References Cited

OTHER PUBLICATIONS

Final Office Action in U.S. Appl. No. 16/369,981, mailed Mar. 20, 2020, 20 pages.

* cited by examiner

Fig. 1: Pain intensity difference (PID) scores over time for example-1, example-2, and example-3 over CELEBREX® 200 mg and CELEBREX® 400 mg oral capsules.

Figs. 2A and 2B: Summary of the PD metrics for a proposed initial dose of 175 mg of celecoxib on day 1, followed by subsequent doses of 125 mg of celecoxib after every 8 hours.

* top line – under fasted conditions, bottom line – under fed conditions

METHODS OF TREATING PAIN

CROSS REFERENCE TO RELATED APPLICATIONS

This application claims the benefit of and priority to U.S. Provisional Patent Application No. 63/131,172, filed Dec. 28, 2020, the contents of which are incorporated by reference herein in their entirety.

FIELD OF THE APPLICATION

The present application relates to a method of providing a therapeutic regimen for the treatment of acute pain, wherein said method comprises administering an oral liquid pharmaceutical composition comprising celecoxib or a pharmaceutically acceptable salt thereof to a subject in need thereof.

BACKGROUND

Celecoxib is a non-steroidal anti-inflammatory drug (NSAID), specifically a COX-2 inhibitor, generally used for the treatment of pain. Chemically celecoxib is designated as 4-[5-(4-methylphenyl)-3-(trifluoromethyl)-1H-pyrazol-1-yl] benzenesulfonamide and is a diaryl-substituted pyrazole. The empirical formula is $C_{17}H_{14}F_3N_3O_2S$, and the molecular weight is 381.38; the chemical structure is as follows:

Celecoxib was described in U.S. Pat. No. 5,466,823 assigned to Searle, which is directed to a class of 1, 5-diaryl pyrazoles and their salts, together with processes for the preparation of such compounds.

Celecoxib is approved in the U.S. under the brand name CELEBREX®, as oral capsules and used in the treatment of osteoarthritis, rheumatoid arthritis, juvenile rheumatoid arthritis, ankylosing spondylitis, acute pain, chronic pain, primary dysmenorrhea, and familial adenomatous polyposis. It is available in the strengths of 50 mg, 100 mg, 200 mg, and 400 mg.

Celecoxib is a hydrophobic and highly permeable drug belonging to class II of the biopharmaceutics classification system. The insoluble nature of celecoxib leads to high variability in absorption and hence has limited bioavailability after oral administration. Celecoxib has an aqueous solubility of about 5 µg/ml at between 5° C. and 40° C., which is pH-independent at pH<9. Celecoxib is not readily dissolved and dispersed for rapid absorption in the gastrointestinal tract when administered orally, for example, in capsule form. Oral administration is always associated with a delayed onset for getting the desired pharmacological action. It is known that upon oral administration, celecoxib takes approximately 3.0 hours for peak plasma concentrations and hence has a delayed onset of action after administration. Additionally, the intake of food further influences drug absorption. Also, correct dosing is an added complexity that further affects therapeutically effective plasma drug concentration, wherein safety and efficacy must be balanced upon administration. Additionally, it is always desired to achieve therapeutic serum levels fast enough to receive benefits for acute conditions.

However, acute pain conditions like odontogenic pain, including post-surgical dental pain, dental pulpitis (toothache), and/or tooth sensitivity, demand immediate/faster pain relief with maintained serum concentration of the drug for time. There remains a clear unmet need in the art for the treatment of acute pain conditions, to provide a suitable therapeutic regimen for celecoxib with faster pain relief, and with minimal or reduced adverse events.

Accordingly, the present application relates to a method of providing a therapeutic regimen for the treatment of acute pain, wherein said method comprises administering an oral liquid pharmaceutical composition comprising celecoxib or a pharmaceutically acceptable salt thereof to a subject in need thereof.

SUMMARY

In one embodiment, the present application provides a method of providing a therapeutic regimen for the treatment of pain, wherein said method comprises administering an oral liquid pharmaceutical composition comprising celecoxib or a pharmaceutically acceptable salt thereof, to a subject in need thereof.

In another embodiment, the present application provides a method of treating or ameliorating or reducing acute pain condition comprising administering an oral liquid pharmaceutical composition comprising celecoxib or a pharmaceutically acceptable salt thereof, to a subject in need thereof, wherein said method offers significantly similar or lesser incidence of treatment-emergent adverse events compared to placebo therapy.

In an aspect of the above embodiments, the oral liquid pharmaceutical composition comprising celecoxib is administered with or without food.

DETAILED DESCRIPTION OF THE APPLICATION

The details of one or more embodiments of the present invention are set forth in this document. Modifications to embodiments described in this document, and other embodiments, will be evident to those of ordinary skill in the art after studying the information provided in this document. The information provided in this document, and particularly the specific details of the described exemplary embodiments, is provided primarily for clearness of understanding and no unnecessary limitations are to be understood therefrom.

Unless otherwise defined, all technical and scientific terms used herein have the same meaning as commonly understood by one of ordinary skill in the art.

Definitions: The terms as used herein have the following meanings:

The term "comprising," as used herein, is open-ended and means the elements recited, or their equivalent in structure or function, plus any other element or elements which are not recited. The terms "having" and "including" are also to be construed as open-ended unless the context suggests otherwise. These terms are not in the exclusive sense of "consisting only of." All ranges recited herein include the endpoints, including those that recite a range "between" two values.

The terms "a," and "the," as used herein, are understood to encompass the plural as well as the singular or otherwise clearly mentioned wherever needed. For example, "an excipient" includes one or more of such excipients, and "the carrier" includes one or more of such carriers.

The terms such as "about," "up to," "generally," and the like as used herein, are to be construed as modifying a term or value such that it is not absolute. Such terms will be defined by the circumstances, and the terms that they modify as those terms are understood by those skilled in the art. This includes, at very least, the degree of expected experimental error, technical error, and instrumental error for a given experiment, technique, or instrument used to measure value. The term "about" is used to provide flexibility to a numerical range endpoint by providing that a given value may be "a little above" or "a little below" the endpoint. As used herein, the term "about" means a slight variation of the value specified, within 10% of the value specified. Nevertheless, the term "about" can mean a higher tolerance of variation depending on, for instance, the experimental technique used. Said variations of a specified value are understood by the skilled person and are within the context of the present invention. As an illustration, a numerical range of "about 1 to about 5" should be interpreted to include not only the explicitly recited values of about 1 to about 5 but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, 5, or 6, individually. This same principle applies to ranges reciting only one numerical value as a minimum or a maximum.

The terms "effective amount," or "therapeutically effective amount," or "therapeutically effective concentration," as used herein, refer to a non-toxic but sufficient amount of the drug in the skin tissue to achieve therapeutic results in treating a condition for which the drug is known to be effective, but low enough to avoid serious side effects (at a reasonable benefit/risk ratio), within the scope of sound medical judgment. The effective amount of the active agent or a pharmaceutically acceptable salt will vary with the particular condition being treated, the age and physical condition of the patient being treated, the severity of the condition, and the duration of the treatment, the nature of concurrent therapy, and like factors within the knowledge and expertise of the attending physician. In this instance, an effective amount is an amount of celecoxib, which is sufficient to treat pain in a patient in need thereof, which is to say, to provide some analgesia measure to reduce or partially reduce the patient's perception of pain.

The term "at least," as used herein, refers to the presence of the recited substance in the composition in the recited least amount.

The terms "excipient," or "pharmaceutically acceptable excipient," as used herein, are used interchangeably to mention any pharmaceutically acceptable material or a component of the composition that is not having any pharmacological effect, which is acceptable for use in pharmaceutical compositions and does not provide any therapeutic effect, and may contribute to physicochemical properties or any relevant nontherapeutic function of the composition. The excipients useful in preparing a pharmaceutical composition are generally safe, non-toxic, do not interact with other components of a composition in a deleterious manner, and are acceptable for human or veterinary use. The term "excipient" or a "topically acceptable excipient" used in the specification includes both one and more than one such excipient.

The terms "agent," "excipient," "ingredient," "substance," and "compound" as used herein, encompass both the singular and plural forms to indicate one or more such agents, excipients, ingredients, substances, or compounds.

The terms "drug," "active," "active agent," and "pharmaceutical," as used herein, are used interchangeably to refer to a pharmacologically active substance or composition. These terms of art are well-known in the pharmaceutical and medicinal arts. In certain aspects, these terms are also interchangeably used with the term "celecoxib or a pharmaceutically acceptable salt thereof."

The term "pharmaceutically acceptable salt," as used herein, includes derivatives of the disclosed compounds within the scope of sound medical judgment, suitable for use in humans and lower animals without undue toxicity, irritation, allergic response, and the like, which are well known in the art. The salt can be prepared in situ during the final isolation and purification of the compounds of the invention, or separately by the pharmaceutically active substance's reaction, having a freebase function, with a suitable organic or inorganic acid. Further, the term refers to pharmaceutically acceptable solvates, including hydrates, of such compounds and such salt.

The terms "pharmaceutical composition," "composition," and "formulation," as used herein, are used interchangeably and refer to a mixture of two or more compounds, elements, or molecules. Also, the terms "composition" and "formulation" may be used to refer to a mixture of the active agent(s) with one or more excipients or other carriers, containing a mixture of two or more compounds, elements, or molecules. Furthermore, the term "dosage form" can include one or more composition(s) or formulation(s) provided in a format for oral administration to a subject like a solution, suspension, emulsion, dispersion, liquid mixture, and the like.

The term "treating," as used herein, includes treatment and/or prophylaxis of a physical and/or mental condition, or amelioration or elimination of the developed condition once it has been established, or alleviation of the characteristic symptoms of such condition.

The term "celecoxib," as used herein, encompasses base form as well as its pharmaceutically acceptable salts, complexes, polymorphs, hydrates, solvates, enantiomers, or racemates. The solid-state form of celecoxib used in the composition of the present application is not critical. For example, celecoxib can be amorphous or crystalline.

The term "$C_{max}$," as used herein, refers to maximum plasma concentration of celecoxib attained on day 1 upon administering the present therapeutic regimen for the treatment of pain under fasting or fed conditions.

The term "$C_{min}$," as used herein, refers to minimum plasma concentration of celecoxib attained on day 1 upon administering the present therapeutic regimen for the treatment of pain under fasting or fed conditions.

The term "odontogenic pain," as used herein, refers to pain initiating from teeth or their supporting structures, including mucosa, gingivae, maxilla, mandible, or periodontal area and the like.

The term "pain relief," as used herein, refers to a patient report of pain intensity≥1 level lower than the pre-dose rating on a 5-point categorical pain relief scale (where 0=no pain relief, 1=little pain relief, 2=some pain relief, 3=a lot of pain relief, 4=complete pain relief). Total Pain Relief (TOTPAR) refers to the patient report of pain intensity=4 over the first 2 hours (TOTPAR2), 4 hours (TOTPAR4), 6 hours (TOTPAR6), and 8 hours (TOTPAR8) using the same scale.

The term "pain intensity difference (PID)," as used herein, refers to pain intensity characterized on a 4-point categorical pain intensity (PI) scale (0=none, 1=mild, 2=moderate, 3=severe). A score of ≥5, on the 11-point Numerical Pain Rating Scale (NPRS) where 0 represents 'no pain' and 10 represents 'worst pain imaginable.' It is measured as Pain intensity Difference at time t $(PID_t)=PI_0-PI_t$, where t is 15 minutes, 30 minutes, 45 minutes, 1 hour, 1.5 hours, 2 hours, 3 hours, 4 hours, 5 hours, 6 hours, 7 hours, or 8 hours.

The term "summed pain intensity difference (SPID)," as used herein, refers to the summation of the time-weighted difference in the pain intensity scores (pain intensity difference or PID) at each nominal time point over baseline, over the first 2 hours (SPID2), 4 hours (SPID4), 6 hours (SPID6) and 8 hours (SPID8) post-dose, for each of the doses of the present pharmaceutical composition of celecoxib in comparison to placebo.

The terms "perceptible pain relief," and "meaningful pain relief," as used herein, refer to subjective terms and recorded as a time to the subjects' first perceived pain relief (onset of pain relief) and when they first experience meaningful pain relief, respectively. In some embodiments, such terms are measured using the 'two stopwatch' method generally known in the art.

The term "satisfactoriness of the treatment," as used herein, refers to the performance of the drug administered to treat pain, evaluated as the rate of pain control post-dose, wherein the assessment is done after 8 hours of treatment initiation or at least 5 minutes prior to the first dose of rescue medication and/or early discontinuation. Subjects reporting a score of '2' or higher using a 5-point verbal rating scale (where 0=poor, 1=fair, 2=good, 3=very good, or 4=excellent) are considered to be satisfied with the treatment received.

The term "rescue medication," as used herein, refers to any medications, other than a study medication, taken for treating or alleviating, or reducing acute pain condition such as odontogenic pain after taking the first dose of the study medication. Rescue medications typically include but are not limited to opioids such as oxycodone, hydrocodone, codeine, or morphine; acetaminophen; aspirin; ibuprofen; or diclofenac.

The term "subject," as used herein, refers to a human who may or may not be suffering from acute odontogenic pain conditions such as pain including post-surgical dental pain, dental pulpitis (toothache), and/or tooth sensitivity.

The term "patient," as used herein, refers to a human who may be suffering from acute odontogenic pain conditions such as pain including post-surgical dental pain, dental pulpitis (toothache), and/or tooth sensitivity.

The terms "conventional celecoxib oral composition" and "conventional composition," as used herein, refer to oral celecoxib capsules marketed under the brand name CELEBREX® by G.D. Searle LLC in the US or its pharmaceutical equivalents or its therapeutic equivalents or later approved drugs which are designated as AB-rated by US FDA as per Approved Drug Products with Therapeutic Equivalence Evaluations (34th edition), or drugs obtained marketing approval by US FDA through Abbreviated New Drug Application (ANDA) filing by establishing bioequivalence to such product. In some embodiments, CELEBREX® includes its US FDA approved therapeutic or pharmaceutical equivalents, available in the strengths of 200 mg and 400 mg. CELEBREX® is a Trademark registered and owned by G.D. Searle LLC (Division of Pfizer Inc. NY), NY 10017, USA.

The term "therapeutic regimen" or "dosing regimen," as used herein, are used interchangeably, and herein refers to a dose of celecoxib or a pharmaceutically acceptable salt thereof and a frequency of administration, wherein said therapeutic regimen is administered to a subject in need thereof to achieve the intended treatment or effect.

The term "pharmacometric analysis," as used herein, refers to pharmacokinetic/pharmacodynamics (PK/PD) modeling studies, including development and qualification of the population pharmacokinetic (PK) model and exposure-response (E-R) model based on the oral liquid pharmaceutical composition of celecoxib administered to the subjects in need thereof, under fasted and fed conditions. In some embodiments, "pharmacometric analysis" also refers to the derivation of the drug exposure targets under single and multiple dosing, simulation of alternate dose and dosing regimens, and comparison of exposure metrics with that of the drug exposure targets and dosing regimens.

In one embodiment, the present application relates to a method of providing a therapeutic regimen for the treatment of pain, wherein said method comprises administering an oral liquid pharmaceutical composition comprising celecoxib or a pharmaceutically acceptable salt thereof, to a subject in need thereof.

In an embodiment, the present application relates to a method of providing a therapeutic regimen for the treatment of acute pain, wherein said method comprises administering an oral liquid pharmaceutical composition comprising celecoxib or a pharmaceutically acceptable salt thereof, to a subject in need thereof.

In an embodiment, the present application relates to a method of providing a therapeutic regimen for the treatment of chronic pain, wherein said method comprises administering an oral liquid pharmaceutical composition comprising celecoxib or a pharmaceutically acceptable salt thereof, to a subject in need thereof.

In another embodiment, the present application relates to a method of providing a therapeutic regimen for the treatment of pain (e.g., acute pain), wherein said method comprises administering an oral liquid pharmaceutical composition comprising celecoxib or a pharmaceutically acceptable salt thereof, to a subject in need thereof, wherein said therapeutic regimen maintains steady-state maximum plasma concentration ($C_{maxss}$) of not more than about 1400 ng/mL upon oral administration under fasting conditions.

In yet another embodiment, the present application relates to a method of providing a therapeutic regimen for the treatment of pain (e.g., acute pain), wherein said method comprises administering an oral liquid pharmaceutical composition comprising celecoxib or a pharmaceutically acceptable salt thereof, to a subject in need thereof, wherein said therapeutic regimen maintains steady-state maximum plasma concentration ($C_{maxss}$) of not more than about 1150 ng/mL upon oral administration under fed conditions.

In an aspect of the above embodiments, the present method provides a therapeutic regimen for the treatment of pain (e.g., acute pain), wherein said therapeutic regimen provides steady-state maximum plasma concentration ($C_{maxss}$) of celecoxib is at least about 2 fold higher than conventional 400 mg followed by 200 mg every 12 hours celecoxib oral capsules upon oral administration under fasting conditions.

In another aspect of the above embodiments, the present method provides a therapeutic regimen for the treatment of pain (e.g., acute pain), wherein said therapeutic regimen provides steady-state maximum plasma concentration ($C_{maxss}$) of celecoxib is at least about 2 fold, about 3 fold, or about 4 fold higher than conventional 400 mg followed by 200 mg every 12 hours celecoxib oral capsules upon oral administration under fasting conditions.

In another aspect of the above embodiments, the present method provides a therapeutic regimen for the treatment of pain (e.g., acute pain), wherein said therapeutic regimen maintains steady-state maximum plasma concentration ($C_{maxss}$) of not more than about 1400 ng/ml, about 1350 ng/ml, about 1300 ng/ml, about 1250 ng/ml, about 1200 ng/ml, about 1150 ng/ml, about 1100 ng/ml, about 1050 ng/ml, about 1000 ng/ml, about 950 ng/ml, or about 900 ng/ml, upon oral administration under fasting conditions.

In yet another aspect of the above embodiments, the present method provides a therapeutic regimen for the treatment of pain (e.g., acute pain), wherein said therapeutic regimen maintains steady-state maximum plasma concentration ($C_{maxss}$) of not more than about 1150 ng/ml, about 1100 ng/ml, about 1050 ng/ml, about 1000 ng/ml, about 950 ng/ml, about 900 ng/ml, about 850 ng/ml, about 800 ng/ml, about 750 ng/ml, or about 700 ng/ml upon oral administration under fed conditions.

In another aspect of the above embodiments, the present method provides a therapeutic regimen for the treatment of pain (e.g., acute pain), wherein said composition upon administration under fasting conditions provides a ratio of $C_{max1}:C_{maxss}$ from about 1:2 to about 1:7.

In another aspect of the above embodiments, the present method provides a therapeutic regimen for the treatment of pain (e.g., acute pain), wherein said composition upon administration under fed conditions provides a ratio of $C_{max1}:C_{maxss}$ from about 1:0 to about 1:5.

In another aspect of the above embodiments, the present method provides a therapeutic regimen for the treatment of pain (e.g., acute pain), wherein said composition upon administration provides a $C_{avg}$ ratio from about 1:0 to about 1:5 under fasting over fed condition.

In an aspect of the above embodiments, the present method provides a therapeutic regimen for the treatment of pain (e.g., acute pain), wherein said therapeutic regimen provides at least about 20% lesser $T_{max}$ than conventional 400 mg celecoxib oral capsules.

In an aspect of the above embodiments, the present method provides a therapeutic regimen for the treatment of pain (e.g., acute pain), wherein said therapeutic regimen provides $T_{max}$ of at least about 1.0 hour upon oral administration under fasting conditions.

In another aspect of the above embodiments, the present method provides a therapeutic regimen for the treatment of pain (e.g., acute pain), wherein said therapeutic regimen provides $T_{max}$ of at least about 1.0 hour, about 1.1 hours, about 1.2 hours, about 1.3 hours, about 1.4 hours, about 1.5 hours about 1.6 hours, or about 1.7 hours upon oral administration under fasting conditions.

In an aspect of the above embodiments, the present method provides a therapeutic regimen for the treatment of pain (e.g., acute pain), wherein said therapeutic regimen provides $T_{max}$ of at least about 2.0 hours upon oral administration under fed conditions.

In another aspect of the above embodiments, the present method provides a therapeutic regimen for the treatment of pain (e.g., acute pain), wherein said therapeutic regimen provides $T_{max}$ of at least about 1.7 hours, about 1.8 hours, about 1.9 hours, about 2.0 hours, about 2.1 hours, about 2.2 hours, about 2.3 hours, about 2.4 hours, or about 2.5 hours upon oral administration under fed conditions.

In an aspect of the above embodiments, the present administration comprises at least about 30% reduced dose of celecoxib than conventional celecoxib composition comprising 400 mg celecoxib oral capsules.

In another aspect of the above embodiments, the present administration comprises at least about 30% to about 40% reduced dose of celecoxib than conventional celecoxib composition comprising 400 mg celecoxib oral capsules.

In an aspect of the above embodiments, the present administration comprises at least about 10% reduced dose of celecoxib than conventional celecoxib composition comprising 200 mg celecoxib oral capsules.

In another aspect of the above embodiments, the present administration comprises at least about 10% to about 40% reduced dose of celecoxib than conventional celecoxib composition comprising 200 mg celecoxib oral capsules.

In an aspect of the above embodiments, the present application relates to a method of treating, ameliorating, or reducing an acute odontogenic pain condition comprising administering an oral liquid pharmaceutical composition comprising celecoxib or a pharmaceutically acceptable salt thereof to a subject in need thereof, wherein said administration comprises at least about 30% reduced dose of celecoxib than conventional celecoxib composition comprising 200 mg celecoxib oral capsules.

In an aspect of the above embodiments, the present application relates to a method of treating, ameliorating, or reducing an acute odontogenic pain condition comprising administering an oral liquid pharmaceutical composition comprising celecoxib or a pharmaceutically acceptable salt thereof to a subject in need thereof, wherein said administration comprises at least about 30% to about 40% reduced dose of celecoxib than conventional celecoxib composition comprising 200 mg celecoxib oral capsules.

In an aspect of the above embodiments, the present administration comprises a dose of about 50 mg to about 320 mg of celecoxib.

In another aspect of the above embodiments, the present administration comprises a dose of about 50 mg, about 60 mg, about 70 mg, about 80 mg, about 90 mg, about 100 mg, about 110 mg, about 120 mg, about 125 mg, about 130 mg, about 140 mg, about 150 mg, about 160 mg, about 170 mg, about 175 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, or about 320 mg of celecoxib.

In another aspect of the above embodiments, the present administration comprises a dose of about 62.5 mg of celecoxib.

In another aspect of the above embodiments, the present administration comprises a dose of about 100 mg of celecoxib.

In another aspect of the above embodiments, the present administration comprises a dose of about 125 mg of celecoxib.

In another aspect of the above embodiments, the present administration comprises a dose of about 175 mg of celecoxib.

In another aspect of the above embodiments, the present administration comprises a dose of about 200 mg of celecoxib.

In another aspect of the above embodiments, the present administration comprises a dose of about 250 mg of celecoxib.

In an aspect of the above embodiments, the present application relates to a method of providing a therapeutic regimen for the treatment of pain (e.g., acute pain), wherein said method comprises administering an oral liquid pharmaceutical composition comprising celecoxib or a pharmaceutically acceptable salt thereof, to a subject in need thereof, wherein said therapeutic regimen comprises administering an initial dose of 175 mg of celecoxib on day 1, followed by subsequent doses of 125 mg of celecoxib after every 8 hours.

In another aspect of the above embodiments, the present application relates to a method of providing a therapeutic regimen for the treatment of pain (e.g., acute pain), wherein said method comprises administering an oral liquid pharmaceutical composition comprising celecoxib or a pharmaceutically acceptable salt thereof, to a subject in need thereof, wherein said therapeutic regimen comprises administering an initial dose of 175 mg of celecoxib on day 1, followed by subsequent doses of 125 mg of celecoxib after every 6 hours.

In yet another aspect of the above embodiments, the present application relates to a method of providing a therapeutic regimen for the treatment of pain (e.g., acute pain), wherein said method comprises administering an oral liquid pharmaceutical composition comprising celecoxib or a pharmaceutically acceptable salt thereof, to a subject in need thereof, wherein said therapeutic regimen comprises administering an initial dose of 200 mg of celecoxib on day 1, followed by subsequent doses of 100 mg of celecoxib after every 6 hours.

In yet another aspect of the above embodiments, the present application relates to a method of providing a therapeutic regimen for the treatment of pain (e.g., acute pain), wherein said method comprises administering an oral liquid pharmaceutical composition comprising celecoxib or a pharmaceutically acceptable salt thereof, to a subject in need thereof, wherein said therapeutic regimen comprises administering an initial dose of 200 mg of celecoxib on day 1, followed by subsequent doses of 100 mg of celecoxib after every 6 hours on day 1, and at least 100 mg of celecoxib after every 8 hours on subsequent days.

In yet another aspect of the above embodiments, the present therapeutic regimen for the treatment of acute pain is simulated using pharmacometric analysis.

In an aspect of the above embodiments, the present application relates to a method of providing a therapeutic regimen for the treatment of chronic pain, wherein said method comprises administering an oral liquid pharmaceutical composition comprising celecoxib or a pharmaceutically acceptable salt thereof, to a subject in need thereof, wherein said therapeutic regimen comprises administering an initial dose of 175 mg of celecoxib on day 1, followed by subsequent doses of 125 mg of celecoxib after every 8 hours.

In another aspect of the above embodiments, the present application relates to a method of providing a therapeutic regimen for the treatment of chronic pain, wherein said method comprises administering an oral liquid pharmaceutical composition comprising celecoxib or a pharmaceutically acceptable salt thereof, to a subject in need thereof, wherein said therapeutic regimen comprises administering an initial dose of 175 mg of celecoxib on day 1, followed by subsequent doses of 125 mg of celecoxib after every 6 hours.

In yet another aspect of the above embodiments, the present application relates to a method of providing a therapeutic regimen for the treatment of chronic pain, wherein said method comprises administering an oral liquid pharmaceutical composition comprising celecoxib or a pharmaceutically acceptable salt thereof, to a subject in need thereof, wherein said therapeutic regimen comprises administering an initial dose of 200 mg of celecoxib on day 1, followed by subsequent doses of 100 mg of celecoxib after every 6 hours.

In yet another aspect of the above embodiments, the present application relates to a method of providing a therapeutic regimen for the treatment of chronic pain, wherein said method comprises administering an oral liquid pharmaceutical composition comprising celecoxib or a pharmaceutically acceptable salt thereof, to a subject in need thereof, wherein said therapeutic regimen comprises administering an initial dose of 200 mg of celecoxib on day 1, followed by subsequent doses of 100 mg of celecoxib after every 6 hours on day 1, and at least 100 mg of celecoxib after every 8 hours on subsequent days.

In yet another aspect of the above embodiments, the present therapeutic regimen for the treatment of chronic pain is simulated using pharmacometric analysis.

In an aspect of the above embodiments, the present therapeutic regimen for the treatment of pain comprises administering an oral liquid pharmaceutical composition comprising celecoxib or a pharmaceutically acceptable salt thereof to a subject in need thereof with mild pain, for at least about two days.

In another aspect of the above embodiments, the present therapeutic regimen for the treatment of pain comprises administering an oral liquid pharmaceutical composition comprising celecoxib or a pharmaceutically acceptable salt thereof to a subject in need thereof with moderate pain, for at least about two days.

In yet another aspect of the above embodiments, the present therapeutic regimen for the treatment of pain comprises administering an oral liquid pharmaceutical composition comprising celecoxib or a pharmaceutically acceptable salt thereof, to a subject in need thereof with severe pain, for at least about two days.

In an aspect of the above embodiments, the present therapeutic regimen for the treatment of acute pain comprises administering an oral liquid pharmaceutical composition comprising celecoxib or a pharmaceutically acceptable salt thereof, to a subject in need thereof, for at least about two days.

In another aspect of the above embodiments, the present therapeutic regimen for the treatment of acute pain comprises administering an oral liquid pharmaceutical composition comprising celecoxib or a pharmaceutically acceptable salt thereof, to a subject in need thereof, for at least about two days, three days, four days, five days, six days, or seven days.

In an aspect of the above embodiments, the present therapeutic regimen for the treatment of chronic pain comprises administering an oral liquid pharmaceutical composition comprising celecoxib or a pharmaceutically acceptable salt thereof, to a subject in need thereof, for at least about two days.

In another aspect of the above embodiments, the present therapeutic regimen for the treatment of chronic pain comprises administering an oral liquid pharmaceutical composition comprising celecoxib or a pharmaceutically acceptable salt thereof, to a subject in need thereof, for at least about two days, three days, four days, five days, six days, or seven days.

In another aspect of the above embodiments, the present therapeutic regimen for the treatment of chronic pain comprises administering an oral liquid pharmaceutical composition comprising celecoxib or a pharmaceutically acceptable salt thereof to a subject in need thereof, In some aspects of the above embodiments, the present application relates to a method of providing a therapeutic regimen for the treatment of pain, wherein said pain is selected from, but not limited to, acute pain, migraine pain, cluster headache, neuropathic pain, post-operative pain, chronic lower back pain, herpes neuralgia, phantom limb pain, central pain, odontogenic pain, opioid-resistant pain, visceral pain, surgical pain, bone injury pain, pain during labor and delivery, pain resulting from burns, including sunburn, post-partum pain, angina pain, and genitourinary tract- related pain including cystitis, arthritis pain, inflammation, osteoarthritis, juvenile rheumatoid arthritis, ankylosing spondylitis, primary dysmenorrhea, breakthrough pain, chronic pain or any cancer pain, or any combinations thereof.

In some aspects of the above embodiments, the present application relates to a method of providing a therapeutic regimen for the treatment of acute pain, wherein said acute pain is selected from, but not limited to, migraine pain, cluster headache, post-operative pain, odontogenic pain, pain during labor and delivery, pain resulting from burns, including sunburn, post-partum pain, bone injury pain, or surgical pain, or any combinations thereof.

In some aspects of the above embodiments, the acute pain or acute pain condition is acute odontogenic pain.

In some aspects of the above embodiments, the acute odontogenic pain condition comprises pain associated with post-surgical dental pain, dental pulpitis (toothache), and/or tooth sensitivity and the like or combinations thereof.

In some aspects of the above embodiments, the present application relates to a method of providing a therapeutic regimen for the treatment of chronic pain, wherein said chronic pain is selected from, but not limited to, neuropathic pain, chronic lower back pain, herpes neuralgia, phantom limb pain, central pain, opioid-resistant pain, visceral pain, angina pain, and genitourinary tract- related pain including cystitis, arthritis pain, inflammation, osteoarthritis, rheumatoid arthritis, juvenile rheumatoid arthritis, primary dysmenorrhea, or ankylosing spondylitis, or any combinations thereof.

In an embodiment, the present application relates to a method of treating, ameliorating, or reducing an acute odontogenic pain condition comprising administering an oral liquid pharmaceutical composition comprising celecoxib or a pharmaceutically acceptable salt thereof to a subject in need thereof, wherein said method provides at least one of the following clinical endpoints when compared to conventional 400 mg celecoxib oral capsules:
  a. at least about 20% faster to achieve perceptible pain relief; and
  b. at least about 10% faster to achieve meaningful pain relief.

In another embodiment, the present application relates to a method of treating, ameliorating, or reducing acute odontogenic pain condition comprising administering an oral liquid pharmaceutical composition comprising celecoxib or a pharmaceutically acceptable salt thereof to a subject in need thereof, wherein said method provides at least one of the following clinical endpoints when compared to conventional 200 mg celecoxib oral capsules:
  a. at least about 20% faster to achieve perceptible pain relief; and
  b. at least about 20% faster to achieve meaningful pain relief.

In another embodiment, the present application relates to a method of treating, ameliorating, or reducing acute odontogenic pain condition comprising administering an oral liquid pharmaceutical composition comprising celecoxib or a pharmaceutically acceptable salt thereof to a subject in need thereof, wherein said method provides at least one of the following pain intensity difference (PID) scores over time when compared to conventional 400 mg celecoxib oral capsules:
  a. at least about 5 fold higher at 30 minutes;
  b. at least about 2 fold higher at 1 hour;
  c. at least about 1.5 fold higher at 2 hours; and
  d. at least about 1.5 fold higher at 4 hours.

In another embodiment, the present application relates to a method of treating, ameliorating, or reducing acute odontogenic pain condition comprising administering an oral liquid pharmaceutical composition comprising celecoxib or a pharmaceutically acceptable salt thereof to a subject in need thereof, wherein said method provides at least one of the following pain intensity difference (PID) scores over time when compared to conventional 200 mg celecoxib oral capsules:
  a. at least about 2 fold higher at 30 minutes;
  b. at least about 2 fold higher at 1 hour;
  c. at least about 1.5 fold higher at 2 hours; and
  d. at least about 1.5 fold higher at 4 hours.

In yet another embodiment, the present application relates to a method of treating, ameliorating, or reducing an acute odontogenic pain condition comprising administering an oral liquid pharmaceutical composition comprising celecoxib or a pharmaceutically acceptable salt thereof to a subject in need thereof, wherein said method provides at least one of the following clinical endpoints:
  a. at least about 60% of treated subjects achieving a 50% reduction in their pain intensity score at baseline;
  b. total pain relief (TOTPAR) score at 6 hours post-dose of at least about 600;
  c. total pain relief (TOTPAR) score at 8 hours post-dose of at least about 800;
  d. rescue medication use at 8 hours post-dose in not more than about 25% of subjects;
  e. first use of rescue medication is not more than about 7 hours; and
  f. satisfactoriness of treatment in at least about 60% of subjects.

In another aspect of the above embodiments, said method provides at least one of the following summed pain intensity difference (SPID) scores:
  a. at 2 hours post-dose of at least about 250;
  b. at 6 hours post-dose of at least about 1000; and
  c. at 8 hours post-dose of at least about 1400.

In another embodiment, the present application relates to a method of treating, ameliorating, or reducing an acute odontogenic pain condition comprising administering an oral liquid pharmaceutical composition comprising celecoxib or a pharmaceutically acceptable salt thereof to a subject in need thereof, wherein said method provides at least one of the following summed pain intensity difference (SPID) scores:
  a. at 2 hours post-dose of at least about 250;
  b. at 6 hours post-dose of at least about 1000; and
  c. at 8 hours post-dose of at least about 1400.

In an embodiment, the present application relates to a method of treating, ameliorating, or reducing an acute odontogenic pain condition comprising administering an oral liquid pharmaceutical composition comprising about 50 mg to about 320 mg of celecoxib or a pharmaceutically acceptable salt thereof to a subject in need thereof.

In an embodiment, the present application relates to a method of treating, ameliorating, or reducing an acute odontogenic pain condition comprising administering an oral liquid pharmaceutical composition comprising 62.5 mg of celecoxib or a pharmaceutically acceptable salt thereof to a subject in need thereof.

In an embodiment, the present application relates to a method of treating, ameliorating or reducing an acute odontogenic pain condition comprising administering an oral liquid pharmaceutical composition comprising 100 mg of celecoxib or a pharmaceutically acceptable salt thereof to a subject in need thereof.

In an embodiment, the present application relates to a method of treating, ameliorating or reducing an acute odontogenic pain condition comprising administering an oral liquid pharmaceutical composition comprising 125 mg of celecoxib or a pharmaceutically acceptable salt thereof to a subject in need thereof.

In an embodiment, the present application relates to a method of treating, ameliorating or reducing an acute odontogenic pain condition comprising administering an oral liquid pharmaceutical composition comprising 175 mg of celecoxib or a pharmaceutically acceptable salt thereof to a subject in need thereof.

In an embodiment, the present application relates to a method of treating, ameliorating or reducing an acute odontogenic pain condition comprising administering an oral liquid pharmaceutical composition comprising 200 mg of celecoxib or a pharmaceutically acceptable salt thereof to a subject in need thereof.

In an embodiment, the present application relates to a method of treating, ameliorating or reducing an acute odontogenic pain condition comprising administering an oral liquid pharmaceutical composition comprising 250 mg of celecoxib or a pharmaceutically acceptable salt thereof to a subject in need thereof.

In an embodiment, the present application relates to a method of treating, ameliorating, or reducing an acute odontogenic pain condition comprising administering an oral liquid pharmaceutical composition comprising celecoxib or a pharmaceutically acceptable salt thereof to a subject in need thereof, wherein said method provides peak pain relief within about 100 minutes post-administration.

In an embodiment, the present application relates to a method of treating, ameliorating, or reducing an acute odontogenic pain condition comprising administering an oral liquid pharmaceutical composition comprising 62.5 mg of celecoxib or a pharmaceutically acceptable salt thereof to a subject in need thereof, wherein said method provides peak pain relief within about 100 minutes post-administration.

In another embodiment, the present application relates to a method of treating, ameliorating, or reducing an acute odontogenic pain condition comprising administering an oral liquid pharmaceutical composition comprising 125 mg of celecoxib or a pharmaceutically acceptable salt thereof to a subject in need thereof, wherein said method provides peak pain relief within about 100 minutes post-administration.

In yet another embodiment, the present application relates to a method of treating, ameliorating, or reducing an acute odontogenic pain condition comprising administering an oral liquid pharmaceutical composition comprising 175 mg of celecoxib or a pharmaceutically acceptable salt thereof to a subject in need thereof, wherein said method provides peak pain relief within about 100 minutes post-administration.

In yet another embodiment, the present application relates to a method of treating, ameliorating, or reducing an acute odontogenic pain condition comprising administering an oral liquid pharmaceutical composition comprising 200 mg of celecoxib or a pharmaceutically acceptable salt thereof to a subject in need thereof, wherein said method provides peak pain relief within about 100 minutes post-administration.

In yet another embodiment, the present application relates to a method of treating, ameliorating, or reducing an acute odontogenic pain condition comprising administering an oral liquid pharmaceutical composition comprising 250 mg of celecoxib or a pharmaceutically acceptable salt thereof to a subject in need thereof, wherein said method provides peak pain relief within about 100 minutes post-administration.

In an embodiment, the present application relates to a method of providing a therapeutic regimen for the treatment of acute pain comprising administering an initial dose of 175 mg of celecoxib on day 1, followed by subsequent doses of 125 mg of celecoxib after every 8 hours, wherein said therapeutic regimen provides pain intensity difference (PID) scores of less than about 1.0 within about 30 minutes.

In another embodiment, the present application relates to a method of providing a therapeutic regimen for the treatment of acute pain comprising administering an initial dose of 175 mg of celecoxib on day 1, followed by subsequent doses of 125 mg of celecoxib after every 6 hours, wherein said therapeutic regimen provides pain intensity difference (PID) scores of less than about 1.0 within about 30 minutes.

In yet another embodiment, the present application relates to a method of providing a therapeutic regimen for the treatment of acute pain comprising administering an initial dose of 200 mg of celecoxib on day 1, followed by subsequent doses of 100 mg of celecoxib after every 6 hours, wherein said therapeutic regimen provides pain intensity difference (PID) scores of less than about 1.0 within about 30 minutes.

In an embodiment, the present application relates to a method of treating, ameliorating, or reducing an acute odontogenic pain condition comprising administering an oral liquid pharmaceutical composition comprising about 50 mg to about 320 mg of celecoxib or a pharmaceutically acceptable salt thereof to a subject in need thereof, wherein said method provides at least one of the following pain intensity difference (PID) scores over time:
  a. at least about 1.0 to about 3 at 30 minutes;
  b. at least about 2.5 to about 5.2 at 1 hour;
  c. at least about 3.5 to about 5.5 at 2 hours; and
  d. at least about 3.8 to about 5.5 at 4 hours.

In an embodiment, the present application relates to a method of treating, ameliorating, or reducing an acute odontogenic pain condition comprising administering an oral liquid pharmaceutical composition comprising 62.5 mg of celecoxib or a pharmaceutically acceptable salt thereof to a subject in need thereof, wherein said method provides at least one of the following pain intensity difference (PID) scores over time:
a. at least about 1.0 to about 1.8 at 30 minutes;
b. at least about 2.5 to about 3.2 at 1 hour;
c. at least about 3.5 to about 4 at 2 hours; and
d. at least about 3.8 to about 4.2 at 4 hours.

In an embodiment, the present application relates to a method of treating, ameliorating, or reducing an acute odontogenic pain condition comprising administering an oral liquid pharmaceutical composition comprising 125 mg of celecoxib or a pharmaceutically acceptable salt thereof to a subject in need thereof, wherein said method provides at least one of the following pain intensity difference (PID) scores over time:
a. at least about 2.0 to about 2.8 at 30 minutes;
b. at least about 3.7 to about 4.8 at 1 hour;
c. at least about 4.4 to about 5.4 at 2 hours; and
d. at least about 4.8 to about 5.4 at 4 hours.

In an embodiment, the present application relates to a method of treating, ameliorating, or reducing an acute odontogenic pain condition comprising administering an oral liquid pharmaceutical composition comprising 250 mg of celecoxib or a pharmaceutically acceptable salt thereof to a subject in need thereof, wherein said method provides at least one of the following pain intensity difference (PID) scores over time:
a. at least about 2.5 to about 3.0 at 30 minutes;
b. at least about 4.5 to about 5.2 at 1 hour;
c. at least about 5.0 to about 5.5 at 2 hours; and
d. at least about 4.5 to about 5.5 at 4 hours.

In an embodiment, the present application relates to a method of providing a therapeutic regimen for the treatment of acute pain, wherein said method comprises administering an oral liquid pharmaceutical composition comprising celecoxib or a pharmaceutically acceptable salt thereof, wherein said therapeutic regimen comprising administering an initial dose of 175 mg of celecoxib on day 1, followed by subsequent doses of 125 mg of celecoxib after every 8 hours, provides at least one of the following pharmacokinetic parameters under fasting conditions:
a. $C_{max}$ value of not more than about 1800 ng/ml;
b. $C_{min}$ value on day 1 of not more than about 250 ng/ml;
c. $C_{maxss}$ value of not more than about 1600 ng/ml;
d. $C_{minss}$ value on day 2 and subsequent days of not more than about 300 ng/ml;
e. $C_{avg24}$ value of not more than about 700 ng/ml;
f. $AUC_{ss24}$ value of not more than about 16000 ng/ml; and
g. $T_{max}$ value of at least about 1.0 hour.

In another embodiment, the present application relates to a method of providing a therapeutic regimen for the treatment of acute pain, wherein said method comprises administering an oral liquid pharmaceutical composition comprising celecoxib or a pharmaceutically acceptable salt thereof, wherein said therapeutic regimen comprising administering an initial dose of 175 mg of celecoxib on day 1, followed by subsequent doses of 125 mg of celecoxib after every 8 hours, provides at least one of the following pharmacokinetic parameters under fed conditions:
a. $C_{max}$ value of not more than about 1000 ng/ml;
b. $C_{min}$ value on day 1 of not more than about 250 ng/ml;
c. $C_{maxss}$ value of not more than about 1000 ng/ml;
d. $C_{minss}$ value on day 2 and subsequent days of not more than about 350 ng/ml;
e. $C_{avg24}$ value of not more than about 600 ng/ml;
f. $AUC_{ss24}$ value of not more than about 13000 ng/ml; and
g. $T_{max}$ value of at least about 1.0 hour.

In an embodiment, the present application relates to a method of providing a therapeutic regimen for the treatment of acute pain, wherein said method comprises administering an oral liquid pharmaceutical composition comprising celecoxib or a pharmaceutically acceptable salt thereof, wherein said therapeutic regimen comprising administering an initial dose of 175 mg of celecoxib on day 1, followed by subsequent doses of 125 mg of celecoxib after every 6 hours, provides at least one of the following pharmacokinetic parameters under fasting conditions:
a. $C_{max}$ value of not more than about 1000 ng/ml;
b. $C_{min}$ value on day 1 of not more than about 250 ng/ml;
c. $C_{maxss}$ value of not more than about 1700 ng/ml;
d. $C_{minss}$ value on day 2 and subsequent days of not more than about 500 ng/ml;
e. $C_{avg24}$ value of not more than about 950 ng/ml;
f. $AUC_{ss24}$ value of not more than about 21000 ng/ml; and
g. $T_{max}$ value of at least about 1.0 hour.

In another embodiment, the present application relates to a method of providing a therapeutic regimen for the treatment of acute pain, wherein said method comprises administering an oral liquid pharmaceutical composition comprising celecoxib or a pharmaceutically acceptable salt thereof, wherein said therapeutic regimen comprising administering an initial dose of 175 mg of celecoxib on day 1, followed by subsequent doses of 125 mg of celecoxib after every 6 hours, provides at least one of the following pharmacokinetic parameters under fed conditions:
a. $C_{max}$ value of not more than about 1000 ng/ml;
b. $C_{min}$ value on day 1 of not more than about 400 ng/ml;
c. $C_{maxss}$ value of not more than about 1050 ng/ml;
d. $C_{minss}$ value on day 2 and subsequent days of not more than about 550 ng/ml;
e. $C_{avg24}$ value of not more than about 750 ng/ml;
f. $AUC_{ss24}$ value of not more than about 17500 ng/ml; and
g. $T_{max}$ value of at least about 1.0 hour.

In an embodiment, the present application relates to a method of providing a therapeutic regimen for the treatment of acute pain, wherein said method comprises administering an oral liquid pharmaceutical composition comprising celecoxib or a pharmaceutically acceptable salt thereof, wherein said therapeutic regimen comprising administering an initial dose of 200 mg of celecoxib on day 1, followed by subsequent doses of 100 mg of celecoxib after every 6 hours, provides at least one of the following pharmacokinetic parameters under fasting conditions:
a. $C_{max}$ value of not more than about 2100 ng/ml;
b. $C_{min}$ value on day 1 of not more than about 250 ng/ml;
c. $C_{maxss}$ value of not more than about 1400 ng/ml;
d. $C_{minss}$ value on day 2 and subsequent days of not more than about 400 ng/ml;
e. $C_{avg24}$ value of not more than about 750 ng/ml;
f. $AUC_{ss24}$ value of not more than about 17500 ng/ml; and
g. $T_{max}$ value of at least about 1.0 hour.

In another embodiment, the present application relates to a method of providing a therapeutic regimen for the treatment of acute pain, wherein said method comprises administering an oral liquid pharmaceutical composition comprising celecoxib or a pharmaceutically acceptable salt thereof, wherein said therapeutic regimen comprising administering an initial dose of 200 mg of celecoxib on day 1, followed by subsequent doses of 100 mg of celecoxib after every 6 hours, provides at least one of the following pharmacokinetic parameters under fed conditions:
a. $C_{max}$ value of not more than about 1100 ng/ml;
b. $C_{min}$ value on day 1 of not more than about 450 ng/ml;
c. $C_{maxss}$ value of not more than about 850 ng/ml;

d. $C_{minss}$ value on day 2 and subsequent days of not more than about 450 ng/ml;
e. $C_{avg24}$ value of not more than about 600 ng/ml;
f. $AUC_{ss24}$ value of not more than about 14500 ng/ml; and
g. $T_{max}$ value of at least about 1.0 hour.

In an embodiment, the present application relates to a method of providing a therapeutic regimen for the treatment of acute pain, wherein said method comprises administering an oral liquid pharmaceutical composition comprising celecoxib or a pharmaceutically acceptable salt thereof, wherein said therapeutic regimen comprising administering an initial dose of 200 mg of celecoxib on day 1, followed by subsequent doses of 100 mg of celecoxib after every 6 hours, and at least 100 mg of celecoxib after every 8 hours on subsequent days provides at least one of the following pharmacokinetic parameters under fasting conditions:
a. $C_{max}$ value of not more than about 2100 ng/ml;
b. $C_{min}$ value on day 1 of not more than about 250 ng/ml;
c. $C_{maxss}$ value of not more than about 1400 ng/ml;
d. $C_{minss}$ value on day 2 and subsequent days of not more than about 400 ng/ml;
e. $C_{avg24}$ value of not more than about 750 ng/ml;
f. $AUC_{ss24}$ value of not more than about 17500 ng/ml; and
g. $T_{max}$ value of at least about 1.0 hour.

In another embodiment, the present application relates to a method of providing a therapeutic regimen for the treatment of acute pain, wherein said method comprises administering an oral liquid pharmaceutical composition comprising celecoxib or a pharmaceutically acceptable salt thereof, wherein said therapeutic regimen comprising administering an initial dose of 200 mg of celecoxib on day 1, followed by subsequent doses of 100 mg of celecoxib after every 6 hours, and at least 100 mg of celecoxib after every 8 hours on subsequent days provides at least one of the following pharmacokinetic parameters under fed conditions:
a. $C_{max}$ value of not more than about 1100 ng/ml;
b. $C_{min}$ value on day 1 of not more than about 450 ng/ml;
c. $C_{maxss}$ value of not more than about 850 ng/ml;
d. $C_{minss}$ value on day 2 and subsequent days of not more than about 450 ng/ml;
e. $C_{avg24}$ value of not more than about 600 ng/ml;
f. $AUC_{ss24}$ value of not more than about 14500 ng/ml; and
g. $T_{max}$ value of at least about 1.0 hour.

In an embodiment, the present application relates to a method of treating, ameliorating, or reducing an acute odontogenic pain condition comprising administering an oral liquid pharmaceutical composition comprising about 50 mg to about 320 mg of celecoxib or a pharmaceutically acceptable salt thereof to a subject in need thereof, wherein said method provides at least one of the following pharmacokinetic parameters:
a. $T_{max}$ value ranging from about 1 hour to about 2.5 hours;
b. $C_{max}$ value ranging from about 460 ng/mL to about 2950 ng/mL, and
c. Mean partial AUC at 2 hours ($AUC_{0-2}$) ranges from about 20% to about 40% of mean total AUC ($AUC_{0-\infty}$).

In an embodiment, the present application relates to a method of treating, ameliorating, or reducing an acute odontogenic pain condition comprising administering an oral liquid pharmaceutical composition comprising 62.5 mg of celecoxib or a pharmaceutically acceptable salt thereof to a subject in need thereof, wherein said method provides at least one of the following pharmacokinetic parameters:
a. $T_{max}$ value ranging from about 1.5 hours to about 2.5 hours;
b. $C_{max}$ value ranging from about 460 ng/mL to about 600 ng/mL, and
c. Mean partial AUC at 2 hours ($AUC_{0-2}$) ranges from about 20% to about 30% of mean total AUC ($AUC_{0-\infty}$).

In another embodiment, the present application relates to a method of treating, ameliorating, or reducing an acute odontogenic pain condition comprising administering an oral liquid pharmaceutical composition comprising 125 mg of celecoxib or a pharmaceutically acceptable salt thereof to a subject in need thereof, wherein said method provides at least one of the following pharmacokinetic parameters:
a. $T_{max}$ value ranging from about 1 hour to about 2 hours;
b. $C_{max}$ value ranging from about 1000 ng/mL to about 1500 ng/mL, and
c. Mean partial AUC at 2 hours ($AUC_{0-2}$) ranges from about 25% to about 35% of mean total AUC ($AUC_{0-\infty}$).

In yet another embodiment, the present application relates to a method of treating, ameliorating, or reducing an acute odontogenic pain condition comprising administering an oral liquid pharmaceutical composition comprising 250 mg of celecoxib or a pharmaceutically acceptable salt thereof to a subject in need thereof, wherein said method provides at least one of the following pharmacokinetic parameters:
a. $T_{max}$ value ranging from about 1 hour to about 2 hours;
b. $C_{max}$ value ranging from about 2000 ng/mL to about 2950 ng/mL, and
c. Mean partial AUC at 2 hours ($AUC_{0-2}$) ranges from about 30% to about 40% of mean total AUC ($AUC_{0-\infty}$).

In an embodiment, the present application relates to a method of treating or ameliorating or reducing acute pain conditions comprising administering an oral liquid pharmaceutical composition comprising celecoxib or a pharmaceutically acceptable salt thereof, to a subject in need thereof, wherein said method significantly reduces the incidence of treatment-emergent adverse events.

In an aspect of the above embodiments, the present method of treating or ameliorating or reducing acute pain conditions comprising significantly reducing the incidence of treatment-emergent adverse events, wherein said incidences are significantly similar compared to placebo therapy.

In an aspect of the above embodiments, the present method of treating or ameliorating or reducing acute pain condition comprising significantly reducing the incidence of treatment-emergent adverse events, wherein said treatment-emergent adverse events are selected from one or more of, nausea, vomiting, increased blood bilirubin, dizziness, headache, epistaxis, alveolar osteitis, and associated conditions or events.

In some embodiments, the present application provides oral pharmaceutical compositions comprising a therapeutically effective amount of celecoxib or a pharmaceutically acceptable salt thereof.

In an aspect of the above embodiments, said composition is present in the form of a solution, suspension, emulsion, dispersion, liquid mixture, and the like.

Such dosage forms can be readily adapted to use in the present method of treating, ameliorating, or reducing an acute odontogenic pain condition comprising administering an oral liquid pharmaceutical composition comprising about 50 mg to about 320 mg of celecoxib or a pharmaceutically acceptable salt thereof to a subject in need thereof as described herein.

In some embodiments, the oral liquid compositions of the present application can be dispensed in a liquid form packaged in pharmaceutically acceptable containers with approved closures for oral administration. The liquid composition can be ingested with or without further mixing with aqueous or suitable media before oral administration.

In some embodiments, the oral liquid compositions of the present application can be dispensed in a single-dose or multiple-dose container such as, but not limited to, a sachet, ampoule, syringe, dropper device, tube, or bottle (for example, a tube or bottle that can be squeezed to deliver its contents), optionally as a fixed dosage, the contents of which can be directly orally ingested, or mixed or dispersed into food or liquid.

The present application is further illustrated by the examples provided merely to be exemplary of the pharmaceutical composition described above and do not limit the scope of the application. Certain modifications and equivalents will be apparent to those skilled in the art and are intended to be included within the scope of the present application.

The present invention is illustrated below by reference to the following examples. However, one skilled in the art will appreciate that the specific methods and results discussed are merely illustrative of the present invention and not construed as limiting the application. The following examples may include compilations of data that represent data gathered at various times during development and experimentation related to the present invention.

EXAMPLES

Examples 1-3

The present pharmaceutical compositions comprising celecoxib or a pharmaceutically acceptable salt thereof, may be prepared as described in U.S. Pat. No. 9,572,819, which is incorporated herein in its entirety. Table 1 includes an exemplary composition that can be used in accordance with the method disclosed herein.

TABLE 1

| Ingredients | % w/w |
| --- | --- |
| Celecoxib | 2.475 |
| Lauroyl polyoxyl 32- glycerides (Gelucire 44/14) | 4.125 |
| Glycerol Monocaprylate (Capmul MCM C8) | 4.950 |
| Caprylic/Capric Triglyceride (Captex 300) | 12.376 |
| Polyoxyl 35 Castor Oil (Kolliphor EL) | 24.752 |
| Polyoxyl 40 Hydrogenated Castor Oil (Kolliphor RH 40) | 10.231 |
| Propyl gallate | 0.017 |
| Sweeteners | 8.565 |
| Flavors | 1.444 |
| Menthol | 0.309 |

TABLE 1-continued

| Ingredients | % w/w |
| --- | --- |
| Dehydrated Alcohol (Ethanol) | 19.802 |
| Glycerin | 4.538 |
| Purified water | 6.415 |

The above composition is calculated for specific doses, as shown in below table 2, and packaged in pharmaceutically acceptable containers for oral administration.

TABLE 2

| Example no. | Celecoxib dose |
| --- | --- |
| Example-1 | 62.5 mg |
| Example-2 | 125 mg |
| Example-3 | 250 mg |

Example 4

The pharmaceutical compositions prepared in examples 1-3 were subjected to a randomized, double-blind, placebo-controlled, efficacy, tolerability, safety, and pharmacokinetic studies including various clinical endpoints (primary and secondary) in post-surgical dental pain in 120 subjects following extraction of bilateral mandibular third molars.

Figure 1:
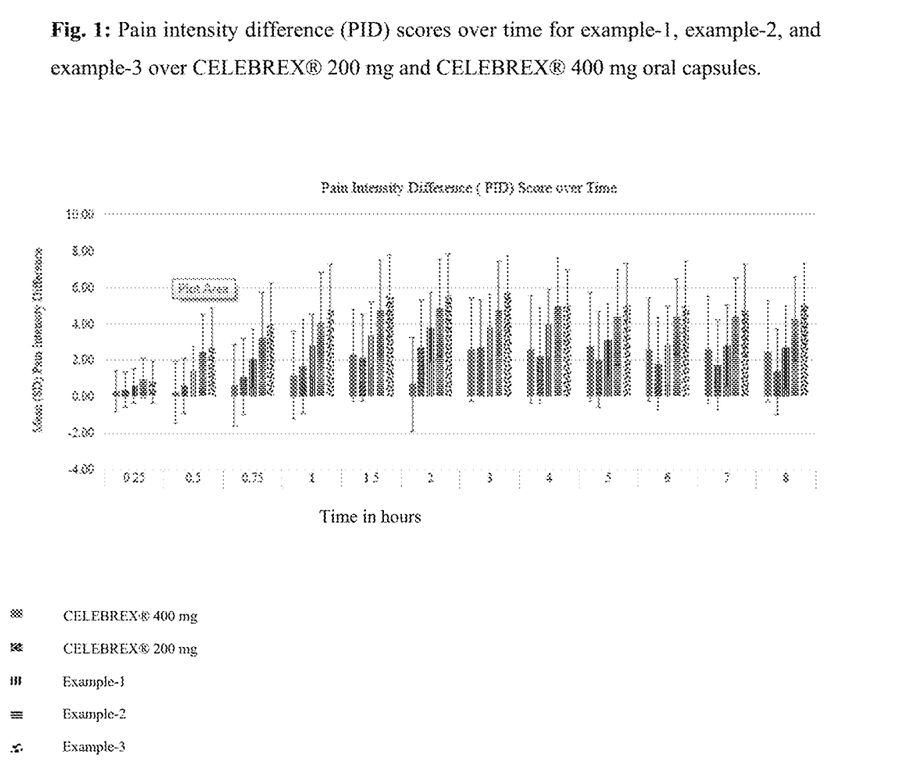
FIG. 1 shows pain intensity difference (PID) scores over time for example-1, example-2, and example-3 over CELEBREX® 200 mg and CELEBREX® 400 mg oral capsules.

The PID scores were measured from the 4-point categorical pain intensity scale to its equivalent score on an 11-point Numeric pain Rating Scale (NPRS) by multiplying the former score with a factor of 2.75 (i.e., 11/4). The results are shown in table 3, table 4, and table 5 below. FIG. 1 shows pain intensity difference (PID) scores over time for example-1, example-2, and example-3 over CELEBREX® 200 mg and CELEBREX® 400 mg oral capsules.

Adverse Events:

Adverse events (AEs) were coded with the Medical Dictionary for Regulatory Activities (MedDRA®) Version 21.0. All AEs captured in the database were listed in by subject data listings, including verbatim term, coded term, treatment, severity, frequency, relationship to treatment, and outcome. Only treatment-emergent Adverse Events (TE-AEs) were summarized.

A TEAE was defined as an AE that started or worsened at the time of or after study drug administration. An AE that occurred during the washout period between drugs was considered treatment-emergent to the last drug given. Suppose an AE that was reported during the study increased in severity, that AE was given a resolution date and time and a new record initiated with the new severity. If the severity of an AE remained the same or decreased, the AE was kept open through to resolution.

TEAEs were tabulated by System Organ Class and Preferred Term. Table 6 includes the number of subjects reporting the AE and as a percent of the number of subjects dosed by treatment.

TABLE 3

| | PID scores and clinical endpoints | | | | | |
| --- | --- | --- | --- | --- | --- | --- |
| Parameters | Example-1 | Example-2 | Example-3 | Placebo | CELEBREX 200 mg | CELEBREX 400 mg |
| Median time to perceptible pain relief (minutes) | 32 | 15 | 20 | 101 | 38 | 43 |

TABLE 3-continued

PID scores and clinical endpoints

| Parameters | Example-1 | Example-2 | Example-3 | Placebo | CELEBREX 200 mg | CELEBREX 400 mg |
|---|---|---|---|---|---|---|
| Median time to meaningful pain relief (minutes) | 114 | 59 | 42 | 232 | 115 | 105 |
| PID score at 15 minutes | 0.60 | 1 | 0.80 | 0.30 | 0.38 | 0.30 |
| PID score at 30 minutes | 1.40 | 2.40 | 2.70 | 0.60 | 0.6 | 0.24 |
| PID score at 45 minutes | 2.10 | 3.30 | 4 | 0.70 | 1.1 | 0.63 |
| PID at 1 hours | 2.80 | 4.10 | 4.80 | 0.90 | 1.65 | 1.18 |
| PID at 1.5 hours | 3.40 | 4.70 | 5.50 | 0.80 | 2.14 | 2.28 |
| PID at 2 hours | 3.80 | 4.90 | 5.60 | 0.80 | 2.72 | 0.68 |
| PID at 3 hours | 3.80 | 4.80 | 5.70 | 1.00 | 2.25 | 2.58 |
| PID at 4 hours | 4.00 | 5.00 | 5.00 | 1.40 | 2.25 | 2.58 |
| PID at 5 hours | 3.10 | 4.40 | 5.00 | 1.50 | 2.03 | 2.75 |
| PID at 6 hours | 2.80 | 4.40 | 4.70 | 4 | 1.81 | 2.58 |
| PID at 7 hours | 2.70 | 4.30 | 5 | 4.30 | 1.76 | 2.58 |
| PID at 8 hours | 2.70 | 4.30 | 5.00 | 4.30 | 1.37 | 2.50 |

TABLE 4

SPID scores and clinical endpoints

| Parameters | Example-1 | Example-2 | Example-3 | Placebo |
|---|---|---|---|---|
| Summed pain intensity difference (SPID) score at 2 hours post-dose | 282.0 | 406.8 | 469.4 | 80.2 |
| Summed pain intensity difference (SPID) score at 6 hours post-dose | 1101.0 | 1509.0 | 1771.7 | 420.2 |
| Summed pain intensity difference (SPID) score at 8 hours post-dose | 1432.1 | 2038.8 | 2352.2 | 866.2 |
| Total pain relief (TOTPAR) score at 6 hours post-dose | 680.4 | 869.8 | 956.1 | 309.5 |
| Total pain relief (TOTPAR) score at 8 hours post-dose | 896.5 | 1171.7 | 1262.9 | 556 |
| Median time to peak pain relief (minutes) | 60 | 60 | 60 | 180 |
| % of subjects reaching perceptible pain relief | 56.7 | 82.8 | 87.1 | 33.3 |
| % of subjects achieving a 50% reduction in pain intensity score at baseline | 73.3 | 86.2 | 93.5 | 36.7 |
| % of subjects using rescue medication at 8 hours post-dose | 23.3 | 10.3 | 6.5 | 53.3 |
| Mean time to first use of rescue medication (minutes) | 395.9 | 414.7 | 321.6 | 197.6 |
| % of subjects with treatment satisfaction | 76.7 | 93.1 | 90.3 | 23.3 |

TABLE 5

Pharmacokinetic parameters

| Parameters | Example-1 | Example-2 | Example-3 |
|---|---|---|---|
| $T_{max}$ (hours) | 1.9 | 1.6 | 1.6 |
| $C_{max}$ (ng/ml) | 548 | 1142 | 2561 |
| % of $AUC_{(0-2)}$ of $AUC_{(0-\infty)}$ | 27% | 30% | 33% |

TABLE 6

Summary of treatment-emergent adverse events

| TEAEs* | Placebo N = 30 n (%) | Treatment A N = 30 n (%) | Treatment B N = 29 n (%) | Treatment C N = 31 n (%) | Overall N = 30 n (%) |
|---|---|---|---|---|---|
| Subjects with at least 1 TEAE, n (%) | 4 (13.3) | 5 (16.7) | 4 (13.8) | 5 (16.1) | 14 (15.6) |
| Gastrointestinal disorders | 2 (6.7) | 2 (6.7) | 1 (3.4) | 1 (3.2) | 4 (4.4) |
| Nausea | 1 (3.3) | 2 (6.7) | 1 (3.4) | 1 (3.2) | 4 (4.4) |
| Vomiting | 1 (3.3) | 1 (3.3) | 0 | 0 | 1 (1.1) |

TABLE 6-continued

Summary of treatment-emergent adverse events

| TEAEs* | Placebo<br>N = 30<br>n (%) | Treatment A<br>N = 30<br>n (%) | Treatment B<br>N = 29<br>n (%) | Treatment C<br>N = 31<br>n (%) | Overall<br>N = 30<br>n (%) |
|---|---|---|---|---|---|
| Investigations | 1 (3.3) | 3 (10.0) | 0 | 2 (6.5) | 5 (5.6) |
| Blood bilirubin increased | 0 | 1 (3.3) | 0 | 2 (6.5) | 3 (3.3) |
| Blood creatinine increased | 1 (3.3) | 0 | 0 | 0 | 0 |
| Blood urine present | 0 | 1 (3.3) | 0 | 0 | 1 (1.1) |
| Cardiac murmur | 0 | 1 (3.3) | 0 | 0 | 1 (1.1) |
| Glomerular filtration rate decreased | 1 (3.3) | 0 | 0 | 0 | 0 |
| Haematocrit decreased | 0 | 1 (3.3) | 0 | 0 | 1 (1.1) |
| Haemoglobon decreased | 0 | 1 (3.3) | 0 | 0 | 1 (1.1) |
| International normalised ratio increased | 0 | 1 (3.3) | 0 | 0 | 1 (1.1) |
| Nervous system disorders | 1 (3.3) | 1 (3.3) | 1 (3.4) | 0 | 2 (2.2) |
| Dizziness | 1 (3.3) | 0 | 1 (3.4) | 0 | 1 (1.1) |
| Headache | 0 | 1 (3.3) | 0 | 0 | 1 (1.1) |
| Infections and infestations | 1 (3.3) | 0 | 1 (3.4) | 0 | 1 (1.1) |
| Alveolar osteitis | 1 (3.3) | 0 | 1 (3.4) | 0 | 1 (1.1) |
| Respiratory, thoracic and mediastinal disorders | 0 | 0 | 0 | 2 (6.5) | 2 (2.2) |
| Epistaxis | 0 | 0 | 0 | 2 (6.5) | 2 (2.2) |
| Blood and lymphatic system disorders | 0 | 0 | 0 | 1 (3.2) | 1 (1.1) |
| Coagulopathy | 0 | 0 | 0 | 1 (3.2) | 1 (1.1) |
| Cardiac disorders | 0 | 0 | 1 (3.4) | 0 | 1 (1.1) |
| Wolff-Parkinson-White syndrome | 0 | 0 | 1 (3.4) | 0 | 1 (1.1) |

*Adverse events are coded using MedDRA Version 21.0
Treatment A: administration of example-1
Treatment B: administration of example-2
Treatment C: administration of example-3

Example 5

Pharmacometric analysis was performed based on pharmacokinetic (PK)-based bridging of the efficacy and safety, exposure-response model was used as supportive evidence and utilized the data from clinical studies as shown in example 4 for the present celecoxib composition than Celebrex® for acute pain indications.

The development and qualification of the population PK model for the present celecoxib composition under fed and fasted conditions used the non-linear mixed-effects modeling estimation algorithm in Pumas v1.0 (Baltimore, MD). A first-order conditional estimation with interaction (FOCE-I) method was used for parameter estimation. The non-compartmental analysis (NCA) results showed that the relative bioavailability of the present celecoxib composition under fed vs. fasted state was 1.03.

The final PK model was qualified using a quantitative predictive check (QPC) approach. The QPC was performed by overlaying the observed 25th, 50th, and 75th percentile of the PK metrics over the distribution of the simulated percentiles of the corresponding PK metrics. The model was deemed qualified, wherein the observed and simulated percentiles of the PK metrics were similar.

The development and qualification of exposure-response (E-R) model for the present celecoxib composition was performed using a sequential modeling approach to relate the individually predicted celecoxib concentrations derived from the population PK model to the time course of pain intensity response measured using the Numerical Pain Rating Scale (NPRS) scores. The E-R model used the 11-point numerical pain rating scale (NPRS) (0=no pain to 10=worst imaginable pain) from the study, as shown in example 4. The E-R analysis was performed using the first-order conditional estimation (FOCE) algorithm in Pumas v1.0 (Baltimore, MD). The pain intensity, recorded longitudinally over 8 hours, using the 11-point NPRS, was modelled using a mixed-effects ordinal logistic regression approach.

The final E-R model was evaluated by Quantitative and Visual Predictive Checks (QPC and VPC). The $50^{th}$ percentile of observed and simulated pain intensity difference (PID) was compared by converting the 11-point NPRS response to a 4-point categorical pain intensity (PI) scale as follows: NPRS score of 0: None (PI=0), 1≤NPRS≤3: Mild (PI=1), 4≤NPRS≤6: Moderate (PI=2) and 7≤NPRS≤10: Severe (PI=3). The PID at a given time t was obtained as PI (baseline)−PI (t).

The alternate dosing regimens for the present celecoxib composition were simulated, as shown in table 7. A total of 22 different dosing regimen scenarios were evaluated for the present celecoxib composition under both fasted and fed conditions upon multiple dosing until 7 days (168 hours).

TABLE 7

Dosing regimen scenarios simulated under fasted and fed conditions

| Q8 regimen (TID)* | Q6 regimen (QID)** |
|---|---|
| 200 mg followed by 175 mg | 200 mg followed by 175 mg |
| 200 mg followed by 150 mg | 200 mg followed by 150 mg |

TABLE 7-continued

Dosing regimen scenarios simulated under fasted and fed conditions

| Q8 regimen (TID)* | Q6 regimen (QID)** |
|---|---|
| 200 mg followed by 125 mg | 200 mg followed by 125 mg |
| 200 mg followed by 100 mg | 200 mg followed by 100 mg |
| 200 mg followed by 75 mg | 200 mg followed by 75 mg |
| 175 mg followed by 150 mg | 175 mg followed by 150 mg |
| 175 mg followed by 125 mg | 175 mg followed by 125 mg |
| 175 mg followed by 100 mg | 175 mg followed by 100 mg |
| 175 mg followed by 75 mg | 175 mg followed by 75 mg |
| 150 mg followed by 150 mg | 150 mg followed by 150 mg |
| 125 mg followed by 125 mg | 125 mg followed by 125 mg |

*Q8 regimen (TID): three times a day after every 8 hours
**Q6 regimen (QID): four times a day after every 6 hours Based on the comparison of PK and clinical efficacy measure of the present celecoxib composition with Celebrex® as described above and using clinical judgment, therapeutic regimens for the present celecoxib composition were proposed using the bridging approach for acute pain indications.

The derived results for the PK metrics for a proposed therapeutic regimen comprising an initial dose of 175 mg of celecoxib on day 1, followed by subsequent doses of 125 mg of celecoxib after every 8 or 6 hours, and 200 mg of celecoxib on day 1, followed by subsequent doses of 100 mg of celecoxib after every 6 hours, with Celebrex® dosing of an initial dose of 400 mg of celecoxib on day 1, followed by subsequent doses of 200 mg of celecoxib after every 12 hours under fasting and fed conditions are shown in table 8, and table 9 respectively.

Figure 2A:
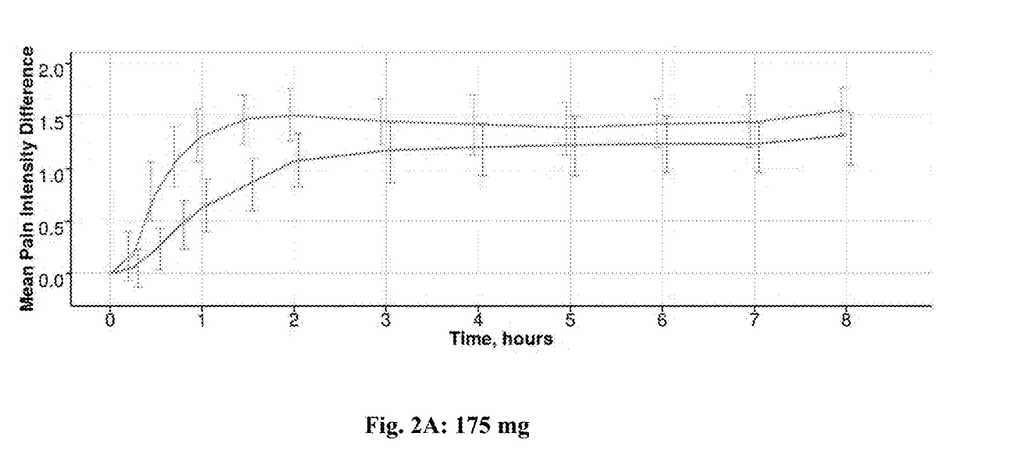
FIG. 2 shows a summary of the pharmacodynamic (PD) metrics for a proposed initial dose of 175 mg of celecoxib on day 1, followed by subsequent doses of 125 mg of celecoxib after every 8 hours.
Figure 2B:
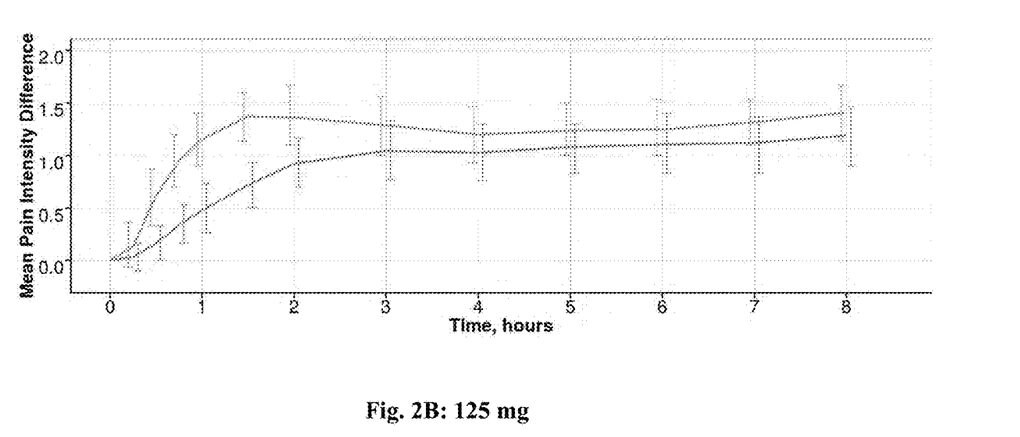

The summary of the PD metrics is shown in FIG. 2 for a proposed initial dose of 175 mg of celecoxib on day 1, followed by subsequent doses of 125 mg of celecoxib after every 8 hours.

TABLE 8

Fasting conditions

| Pharmacokinetic metrics | Therapeutic regimen | | | |
|---|---|---|---|---|
| | 175 mg/125 mg Q8 | 175 mg/125 mg Q6 | 200 mg/100 mg Q6 | CELEBREX® 400 mg/200 mg Q12 |
| $C_{max}$ (ng/ml) | 1632 | 856 | 1865 | 611 |
| (95% CI*) | (1464, 1834) | (761, 951) | (1673, 2096) | (499, 724) |
| $C_{min\#1}$ (ng/ml) | 192 | 217 | 219 | 229 |
| (95% CI) | (159, 235) | (193, 241) | (182, 268) | (183, 276) |
| $C_{maxss}$ (ng/ml) | 1381 | 1496 | 1197 | 532 |
| (95% CI) | (1216, 1580) | (1310, 1721) | (1048, 1377) | (458, 605) |
| $C_{minss}$ (ng/ml) | 256 | 410 | 328 | 232 |
| (95% CI) | (204, 328) | (333, 514) | (266, 411) | (189, 276) |
| $C_{avg24}$ (ng/ml) | 590 | 784 | 627 | 349 |
| (95% CI) | (506, 700) | (672, 929) | (538, 743) | (301, 397) |
| $AUC_{ss24}$ (ng/ml) | 14172 | 18813 | 15051 | 8379 |
| (95% CI) | (12150, 16790) | (16133, 22289) | (12907, 17831) | (7233, 9526) |
| $T_{max}$ (hours) | 1.5 | 1.5 | 1.5 | 2.05 |
| (95% CI) | (1.4, 1.6) | (1.4, 1.6) | (1.4, 1.6) | (2.0, 3.0) |

$C_{min\#}$ = $C_{8h}$ or $C_{6h}$ for the present therapeutic regimens, and $C_{12h}$ for the Celebrex® regimens
CI* = Confidence Interval

TABLE 9

Fed conditions

| Pharmacokinetic metrics | Therapeutic regimen | | | |
|---|---|---|---|---|
| | 175 mg/125 mg Q8 | 175 mg/125 mg Q6 | 200 mg/100 mg Q6 | CELEBREX® 400 mg/200 mg Q12 |
| $C_{max}$ (ng/ml) | 856 | 856 | 978 | 1560 |
| (95% CI) | (761, 951) | (761, 951) | (870, 1087) | (1513, 2109) |
| $C_{min\#1}$ (ng/ml) | 217 | 325 | 372 | 346 |
| (95% CI) | (193, 241) | (290, 366) | (332, 418) | (266, 427) |
| $C_{maxss}$ (ng/ml) | 804 | 924 | 728 | 1114 |
| (95% CI) | (714, 896) | (822, 1066) | (645, 812) | (922, 1306) |
| $C_{minss}$ (ng/ml) | 267 | 435 | 348 | 254 |
| (95% CI) | (231, 303) | (376, 496) | (301, 397) | (177, 331) |
| $C_{avg24}$ (ng/ml) | 481 | 637 | 510 | 560 |
| (95% CI) | (425, 54) | (564, 721) | (451, 576) | (459, 662) |
| $AUC_{ss24}$ (ng/ml) | 11536 | 15294 | 12235 | 13449 |
| (95% CI) | (10209, 13045) | (13536, 17292) | (10829, 13834) | (11012, 15887) |
| $T_{max}$ (hours) | 2.5 | 2.5 | 2.5 | 3.5 |
| (95% CI) | (2.5, 2.6) | (1.4, 1.6) | (2.4, 2.6) | (3.0, 3.7) |

$C_{min\#}$ = $C_{8h}$ or $C_{6h}$ for the present therapeutic regimens, and $C_{12h}$ for the Celebrex® Regimens Example 6

Figure 3:
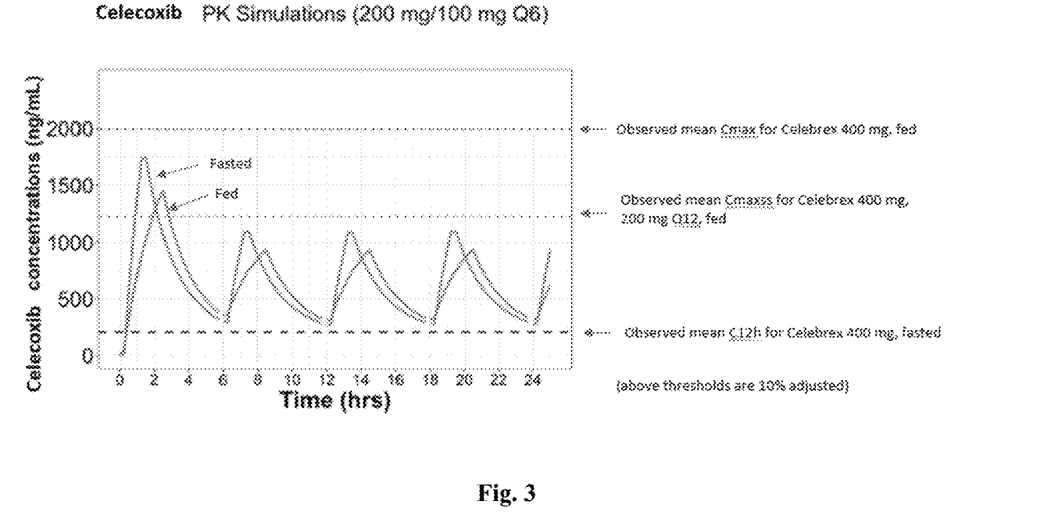
FIG. 3 shows a PK simulation for a proposed initial dose of 200 mg of celecoxib on day 1, followed by subsequent doses of 100 mg of celecoxib after every 6 hours.

Studies were performed to determine the simulated celecoxib levels for the 200 mg/100 mg Q6 dosing regimen. Considering all aspects with respect to meeting the established efficacy and safety targets of Celebrex®, a proposed dosing regimen of celecoxib for acute pain indications is 200 mg followed by 100 mg Q6. FIG. 3 depicts the mean concentration-time profile of the 200 mg/100 mg Q6 regimen, which is well bracketed within the 10% adjusted Celebrex® thresholds at all times over a 24 hour dosing period, and the same trends held over a 7-day dosing period. Studies have shown that the primary efficacy endpoint (SPID6) was met for 62.5 mg, 125 mg and 250 mg against placebo. Thus, the proposed 200 mg/100 mg Q6 can be expected to be efficacious and safe.

What is claimed is:

1. A method of providing a therapeutic regimen for the treatment of acute pain, wherein said method comprises administering an oral liquid pharmaceutical composition comprising celecoxib or a pharmaceutically acceptable salt thereof, to a subject in need thereof, and said therapeutic regimen maintains steady-state maximum plasma concentration ($C_{maxss}$) of not more than about 1400 ng/mL upon oral administration under fasting conditions; wherein said therapeutic regimen comprises administering an initial dose of 200 mg of celecoxib on day 1, followed by subsequent doses of 100 mg of celecoxib after every 6 hours.

2. The method of claim 1, wherein said therapeutic regimen comprises administering an initial dose of 200 mg of celecoxib on day 1, followed by subsequent doses of 100 mg of celecoxib after every 6 hours on day 1, and at least 100 mg of celecoxib after every 8 hours on subsequent days.

3. The method of claim 1, wherein said therapeutic regimen comprises administering an oral liquid pharmaceutical composition comprising celecoxib or a pharmaceutically acceptable salt thereof, to a subject in need thereof, for at least two days.

4. A method of providing a therapeutic regimen for the treatment of pain, wherein said method comprises administering an oral liquid pharmaceutical composition comprising celecoxib or a pharmaceutically acceptable salt thereof, to a subject in need thereof, and said therapeutic regimen maintains steady-state maximum plasma concentration ($C_{maxss}$) of not more than about 1400 ng/ml upon oral administration under fasting conditions; wherein said therapeutic regimen comprises administering an initial dose of 200 mg of celecoxib on day 1, followed by subsequent doses of 100 mg of celecoxib after every 6 hours; wherein said steady-state maximum plasma concentration ($C_{maxss}$) of celecoxib is at least 2 fold higher than conventional 400 mg followed by 200 mg every 12 hours celecoxib oral capsules under fasting condition.

5. The method of claim 1, wherein said therapeutic regimen provides at least 20% lesser $T_{max}$ compared to conventional 400 mg celecoxib oral capsules.

6. The method of claim 1, wherein said therapeutic regimen provides pain intensity difference (PID) scores of less than 1.0 within about 30 minutes.

7. The method of claim 1, wherein said therapeutic regimen is simulated using pharmacometric analysis.

8. The method of claim 1, wherein the pain is acute odontogenic pain.

9. The method of claim 1, wherein said oral liquid pharmaceutical composition is administered with food.

10. A method of treating or ameliorating or reducing an acute pain condition comprising administering an oral liquid pharmaceutical composition comprising celecoxib or a pharmaceutically acceptable salt thereof, to a subject in need thereof, wherein said method offers significantly similar or lesser incidence of treatment-emergent adverse events compared to placebo therapy; wherein said treatment-emergent adverse events are selected from one or more of nausea, vomiting, increased blood bilirubin, dizziness, headache, epistaxis, and alveolar osteitis; and wherein said method comprises a therapeutic regimen comprising administering an initial dose of 200 mg of celecoxib on day 1, followed by subsequent doses of 100 mg of celecoxib after every 6 hours.

11. The method of claim 10, wherein said therapeutic regimen comprises administering an initial dose of 200 mg of celecoxib on day 1, followed by subsequent doses of 100 mg of celecoxib after every 6 hours on day 1, and at least 100 mg of celecoxib after every 8 hours on subsequent days.

12. The method of claim 10, wherein the acute pain condition is acute odontogenic pain.

13. The method of claim 10, wherein said oral liquid pharmaceutical composition is administered with food.

14. The method of claim 1, wherein said oral liquid pharmaceutical composition is administered without food.

15. The method of claim 10, wherein said oral liquid pharmaceutical composition is administered without food.

* * * * *

UNITED STATES PATENT AND TRADEMARK OFFICE
CERTIFICATE OF CORRECTION

PATENT NO. : 12,168,000 B2
APPLICATION NO. : 17/562229
DATED : December 17, 2024
INVENTOR(S) : Munjal et al.

Page 1 of 1

It is certified that error appears in the above-identified patent and that said Letters Patent is hereby corrected as shown below:

In the Claims

In Column 27, in Claim 4, Line 45, delete "ng/ml" and insert -- ng/mL --, therefor.

Signed and Sealed this
Twenty-fifth Day of March, 2025

Coke Morgan Stewart
*Acting Director of the United States Patent and Trademark Office*